(12) United States Patent
Bergman

(10) Patent No.: US 12,138,373 B2
(45) Date of Patent: Nov. 12, 2024

(54) THERMAL PROTECTION SYSTEM FOR A DIALYSATE CONTAINER

(71) Applicant: Fresenius Medical Care Holdings, Inc., Waltham, MA (US)

(72) Inventor: Eric Bergman, Waltham, MA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 922 days.

(21) Appl. No.: 17/123,667

(22) Filed: Dec. 16, 2020

(65) Prior Publication Data

US 2022/0184285 A1 Jun. 16, 2022

(51) Int. Cl.
*A61M 1/16* (2006.01)
*A61M 1/28* (2006.01)

(52) U.S. Cl.
CPC ........ *A61M 1/1668* (2014.02); *A61M 1/1664* (2014.02); *A61M 1/28* (2013.01); *A61M 2205/27* (2013.01); *A61M 2205/584* (2013.01)

(58) Field of Classification Search
CPC .............. A61M 1/1668; A61M 1/1664; A61M 2205/27; Y10T 137/1797; Y10T 137/1812; Y10T 137/1827; Y10T 137/1819; Y10T 137/1804; Y10S 236/05; Y10S 236/12; Y10S 236/00; A61J 1/2027; A61J 1/202;
(Continued)

(56) References Cited

U.S. PATENT DOCUMENTS 2,222,067 A 11/1940 Chaney et al.
4,122,324 A 10/1978 Falk
(Continued)

FOREIGN PATENT DOCUMENTS

CN 102122573 A * 7/2011 ............. Y02E 60/13
CN 204016965 U 12/2014
(Continued)

OTHER PUBLICATIONS

International Search Report and Written Opinion for the International Patent Application No. PCT/US2021/061709, mailed Apr. 6, 2022, 10 pages.

*Primary Examiner* — Leslie A Lopez
*Assistant Examiner* — Seth Han
(74) *Attorney, Agent, or Firm* — KDW Firm PLLC

(57) ABSTRACT

A thermal protection system configured for use with a dialysate container or bag in a dialysis system is disclosed. The thermal protection system being configured so that when the dialysate container is subjected to a temperature greater than a predetermined temperature such as, when the dialysate container is heated within a microwave oven, the thermal protection system is configured to (i) prevent the flow of dialysate from the bag, (ii) indicate that the dialysate container has been subjected to a temperature greater than the predetermined temperature, or (iii) a combination thereof. In one embodiment, the thermal protection system is a circular hollow ring positioned within an exit port of the bag, the ring melting upon reaching the predetermined temperature to block the flow of dialysate. Alternatively, and/or in addition, the thermal protection system may be a thermally sensitive dye configured to change color upon being subjected to the predetermined temperature.

14 Claims, 6 Drawing Sheets

(58) Field of Classification Search
CPC ...... A61J 1/2037; F16K 17/383; F16K 17/03; F16K 17/38
See application file for complete search history.

(56) References Cited

U.S. PATENT DOCUMENTS

| | | | | | |
|---|---|---|---|---|---|
| 4,212,299 | A | * | 7/1980 | Yokokoji | B32B 27/36 604/408 |
| 4,268,738 | A | | 5/1981 | Flautt, Jr. et al. | |
| 4,341,218 | A | * | 7/1982 | U | A61B 17/12136 604/99.04 |
| 4,883,225 | A | * | 11/1989 | Kitchens | G05D 23/1333 236/DIG. 5 |
| 2004/0141886 | A1 | * | 7/2004 | Py | B65B 3/003 141/329 |
| 2004/0154947 | A1 | * | 8/2004 | Duranton | A45D 34/00 206/459.1 |
| 2009/0288662 | A1 | * | 11/2009 | Radford | A61M 16/0003 128/205.24 |
| 2010/0047402 | A1 | | 2/2010 | Birchmeier et al. | |
| 2010/0266322 | A1 | | 10/2010 | Croskey | |
| 2012/0183452 | A1 | | 7/2012 | Schalkhammer | |
| 2015/0045763 | A1 | | 2/2015 | Barone, Jr. et al. | |
| 2016/0194132 | A1 | | 7/2016 | Davidson et al. | |
| 2017/0326282 | A1 | * | 11/2017 | Wilt | A61M 1/362265 |
| 2018/0078665 | A1 | | 3/2018 | Buccellato | |
| 2019/0216997 | A1 | | 7/2019 | Schmidt et al. | |
| 2021/0299337 | A1 | * | 9/2021 | Scott | A61M 1/69 |

FOREIGN PATENT DOCUMENTS

| | | | | |
|---|---|---|---|---|
| CN | 111481759 | A | | 8/2020 |
| JP | H1016053 | A1 | * | 1/1998 ............. B29C 66/71 |
| KR | 20170059601 | A | * | 5/2017 ................ A61J 1/14 |
| WO | WO-2008068508 | A1 | * | 6/2008 ........ A61M 16/0672 |

* cited by examiner

THERMAL PROTECTION SYSTEM FOR A DIALYSATE CONTAINER

FIELD OF THE DISCLOSURE

The disclosure generally relates to dialysis systems, and more particularly to thermal protection for a dialysate container.

BACKGROUND

Dialysis systems and/or machines are known for use in the treatment of renal disease. The two principal dialysis methods are hemodialysis (HD) and peritoneal dialysis (PD). During HD, the patient's blood is passed through a dialyzer of an HD machine while also passing dialysate through the dialyzer. A semi-permeable membrane in the dialyzer separates the blood from the dialysate within the dialyzer and allows diffusion and osmosis exchanges to take place between the dialysate and the blood stream. During PD, the patient's peritoneal cavity is periodically infused with dialysate or dialysis solution. The membranous lining of the patient's peritoneum acts as a natural semi-permeable membrane that allows diffusion and osmosis exchanges to take place between the solution and the blood stream. In Continuous Ambulatory Peritoneal Dialysis (CAPD), patients perform manual exchanges. Automated PD (APD) machines, called PD cyclers, are designed to control the entire PD process so that it can be performed at home, usually overnight, without clinical staff in attendance.

Dialysis systems include one or more dialysate containers or sources such as, for example, bags, for containing a fluid (e.g., a dialysate) for patient infusion. During a treatment operation, dialysate, e.g., fresh and spent dialysate, is moved to and from a patient. For example, dialysate from one or more dialysate bags is moved into the patient's abdomen.

In use, cold dialysate can negatively impact a patient's treatment by making the patient uncomfortable. If the temperature of the dialysate is cold enough patients may start to shiver, which may negatively impact their ability to continue with a treatment session. As such, prior to a treatment session, the dialysate may be heated to an appropriate temperature (e.g., approximately 37 degrees C.). However, if dialysate is warmed significantly hotter than the patient's body temperature, serious thermal injuries can occur to the patient's peritoneum and surrounding internal organs.

Because of the possibility for severe harm, patients are instructed to place the dialysate bag within a bag warming device such as, for example a warming box, or wrapped with a warming wrap. Generally speaking, patients are advised not to immerse the dialysate bag into warm water due to the increased risk of infection and not to place the dialysate bag into a microwave due to the risk of overheating the dialysate. For example, utilization of a microwave to heat the dialysate bag may create hot spots within the dialysate. That is, although the dialysate bag may only feel warm to the patient's touch, a pocket could exist within the dialysate that is significantly hotter.

Nevertheless, despite manufacturer's warnings against microwaving a dialysate bag, articles have been published advising patients to mix a dialysate bag well post microwave. Moreover, despite manufacturer's warnings against microwaving a dialysate bag, articles have been published advising patients that it is acceptable to microwave a dialysate bag. Thus, despite manufacturer's warnings against microwaving a dialysate bag, evidence exists that patients and homecare providers do microwave dialysate bags in order to save time during the heating process.

It is with respect to these and other considerations that the present improvements may be useful.

SUMMARY

This Summary is provided to introduce a selection of concepts in a simplified form that are further described below in the Detailed Description. This Summary is not intended to necessarily identify key features or essential features of the claimed subject matter, nor is it intended as an aid in determining the scope of the claimed subject matter.

According to an exemplary embodiment of the present disclosure, a dialysate container is disclosed. The dialysate container comprises a reservoir arranged and configured to store dialysate, an exit port arranged and configured in fluid communication with the reservoir and arranged and configured to couple to tubing so that dialysate can flow from the reservoir to the tubing, and a thermal protection system arranged and configured in operative communication with the exit port, the thermal protection system arranged and configured so that when the dialysate container is subjected to a temperature greater than a predetermined temperature, the thermal protection system is arranged and configured to prevent the dialysate from flowing through the exit port and into the tubing, or to indicate that the dialysate container has been subjected to a temperature greater than the predetermined temperature, or a combination thereof.

In one embodiment, the thermal protection system is arranged and configured as a circular hollow ring positioned within the exit port of the dialysate container.

In one embodiment, the circular ring comprises a plastic material.

In one embodiment, the circular ring is arranged and configured to melt upon reaching the predetermined temperature, the melted circular ring blocking the dialysate from flowing through the exit port and into the tubing.

In one embodiment, the dialysate container further comprises a support ring having a melting temperature greater than the predetermined temperature so that the support ring guides the melted circular ring to block the dialysate from flowing through the exit port and into the tubing.

In one embodiment, the dialysate container further comprises a metallic wrapping, the metallic wrapping arranged and configured to heat quicker than the circular ring to facilitate faster heating of the circular ring.

In one embodiment, the thermal protection system comprises a thermally sensitive dye arranged and configured to change color upon being subjected to the predetermined temperature to indicate that the dialysate container has been subjected to a temperature greater than the predetermined temperature.

In one embodiment, the thermally sensitive dye is incorporated into a frangible part of the dialysate container.

In one embodiment, the thermal protection system comprises a spring-loaded plunger, the spring-load plunger including a plunger member, a spring, and a holding member, the holding member being arranged and configured to melt upon reaching the predetermined temperature and, upon melting, the holding member releasing the spring causing the plunger member to block the dialysate from flowing through the exit port and into the tubing.

In one embodiment, the plunger member is pivotable from a first position enabling the dialysate to flow through the exit port and into the tubing to a second position blocking the dialysate from flowing through the exit port and into the tubing.

In one embodiment, the plunger member is vertically displaceable from a first position enabling the dialysate to flow through the exit port and into the tubing to a second position blocking the dialysate from flowing through the exit port and into the tubing.

According to an exemplary embodiment of the present disclosure, a dialysate container is disclosed. The dialysate container comprises a reservoir arranged and configured to store dialysate, an exit port arranged and configured in fluid communication with the reservoir and arranged and configured to couple to tubing so that dialysate can flow from the reservoir to the tubing, and a circular hollow ring positioned within the exit port of the dialysate container, the circular hollow ring arranged and configured so that when the dialysate container is subjected to a temperature greater than a predetermined temperature, the circular hollow ring melts to prevent the dialysate from flowing through the exit port and into the tubing, or to indicate that the dialysate container has been subjected to a temperature greater than the predetermined temperature, or a combination thereof.

In one embodiment, the circular ring comprises a plastic material.

In one embodiment, the circular ring is arranged and configured to melt upon reaching the predetermined temperature, the melted circular ring blocking the dialysate from flowing through the exit port and into the tubing.

In one embodiment, the dialysate container further comprises a support ring having a melting temperature greater than the predetermined temperature so that the support ring guides the melted circular ring to block the dialysate from flowing through the exit port and into the tubing.

In one embodiment, the dialysate container further comprises a metallic wrapping, the metallic wrapping arranged and configured to heat quicker than the circular ring to facilitate faster heating of the circular ring.

In one embodiment, the dialysate container further comprises a thermally sensitive dye arranged and configured to change color upon being subjected to the predetermined temperature to indicate that the dialysate container has been subjected to a temperature greater than the predetermined temperature.

In one embodiment, the thermally sensitive dye is incorporated into a frangible part of the dialysate container.

BRIEF DESCRIPTION OF THE DRAWINGS

By way of example, specific embodiments of the disclosed methods and devices will now be described, with reference to the accompanying drawings, in which.

DETAILED DESCRIPTION

Figure 1:
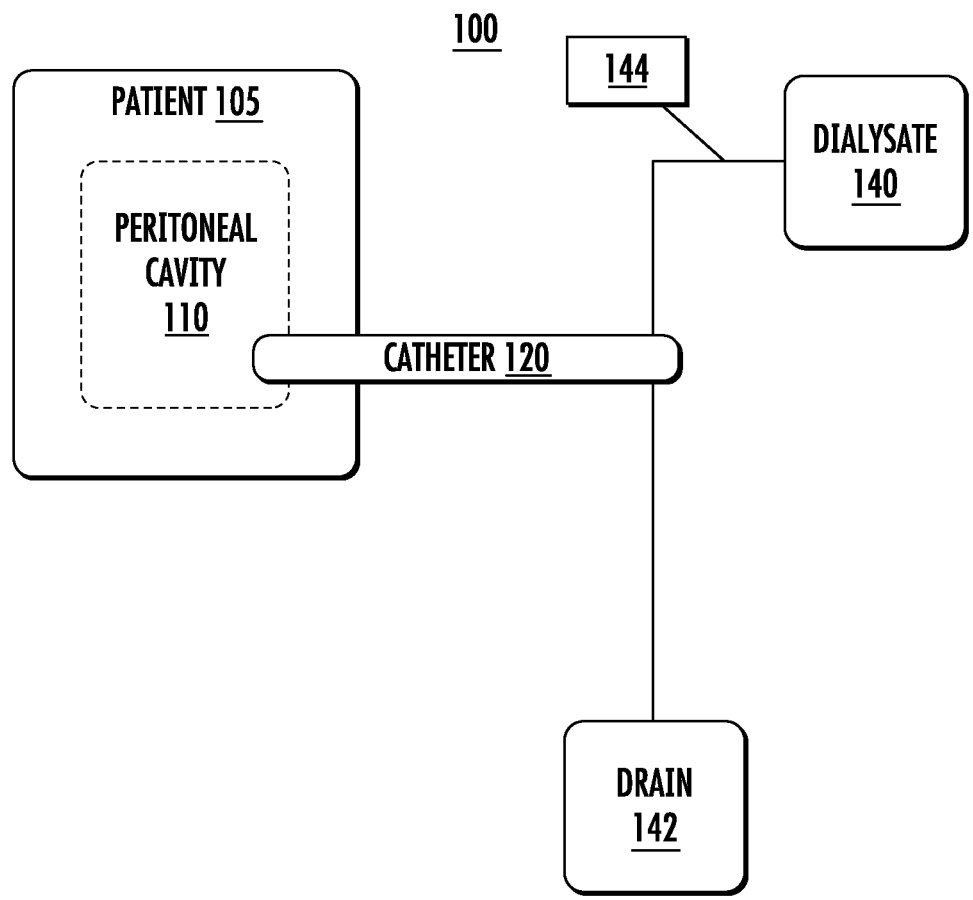
FIG. 1 illustrates an example layout of a continuous ambulatory peritoneal dialysis (CAPD) system.

The present embodiments will now be described more fully hereinafter with reference to the accompanying drawings, in which several exemplary embodiments are shown. The subject matter of the present disclosure, however, may be embodied in many different forms and types of devices and systems for dialysis systems and other potential medical devices and treatments, and should not be construed as limited to the embodiments set forth herein. Rather, these embodiments are provided so that this disclosure will be thorough and complete, and willfully convey the scope of the subject matter to those skilled in the art. In the drawings, like numbers refer to like elements throughout.

Exemplary embodiments of a thermal protection system or device (terms used interchangeably herein without the intent to limit or distinguish) for use in or with dialysate containers (e.g., bags) is disclosed herein. In use, the thermal protection system is arranged and configured to indicate and/or prevent (e.g., stop) usage of the dialysate containers upon determination that the dialysate container has been subjected to extreme temperatures such as, for example, when placed within a microwave oven. That is, in use, the thermal protection system is arranged and configured to inhibit, prevent, etc. the flow of dialysate from the dialysate container upon determination that the dialysate container has been subjected to extreme temperatures such as, for example, when placed within a microwave oven. Alternatively, and/or in addition, the thermal protection system is arranged and configured to indicate to the user that the dialysate container has been subjected to extreme temperatures such as, for example, when placed within a microwave oven FIG. 1 illustrates an example layout of a continuous ambulatory peritoneal dialysis (CAPD) system 100. In use, as will be described herein, the features of the present disclosure are well suited for use in CAPD systems and methods, which are usually performed manually. This is in contrast to APD systems and methods, which may be automated. Nevertheless, it should be appreciated that while the present invention will be illustrated and described in connection with a CAPD system, the present invention should not be so limited. For example, it is envisioned that the present invention may be used in connection with other dialysis systems such as in connection with automated peritoneal dialysis (APD) machines (e.g., PD cyclers). Moreover, it is envisioned that the present invention could be applicable to other areas and devices that require delivery of warmed fluid that should not be heated above a given temperature.

As illustrated in FIG. 1, a patient 105 may have a catheter 120 arranged within a peritoneal cavity 110 of the patient 105. A dialysate container (e.g., a bag) 140 may provide dialysate that may flow from the dialysate container 140 to the catheter 120 via tubing 144. The dialysate may flow through the catheter 120 and into the patient's peritoneal cavity 110. Thereafter, the PD effluent may exit the patient's peritoneal cavity 110 via the catheter 120 and flow to a drain 142.

That is, in use, the CAPD system 100 is arranged and configured to flow fresh dialysate into a patient and drain spent dialysate out of the patient. During treatment, a volume of dialysate may enter the patient's abdomen via the catheter 120 and remain for a period of time, e.g., a dwell time. During the dwell time, the dialysate may flow across the peritoneum and absorb contaminants and/or particulates from a patient's blood and exchange substances and fluids (e.g., electrolytes, urea, glucose, albumin, osmotically active particles, and other small molecules). At the end of the dwell time, the spent dialysate may be flowed out of the patient's abdomen via the catheter 120 and purged to a drain 142 connected to the tubing, e.g., the drain line. This exchange of fresh dialysate and spent dialysate after a dwell time may occur for several cycles depending on the patient's treatment regimen.

One or more dialysate containers 140 may be used during a treatment cycle. In some embodiments, as illustrated, the dialysate container(s) 140 may be a dialysate bag that is hung near the patient. Tubing 144 (e.g., a patient line) may be connected between the dialysate bag 140 and the catheter 120 and may be used to pass dialysate from the dialysate bag 140 to the patient's peritoneal cavity 110. A drain line may be connected to a drain receptacle or drain 142 and may be used to pass dialysate from the catheter 120 to the drain 142 during use.

Figure 2:
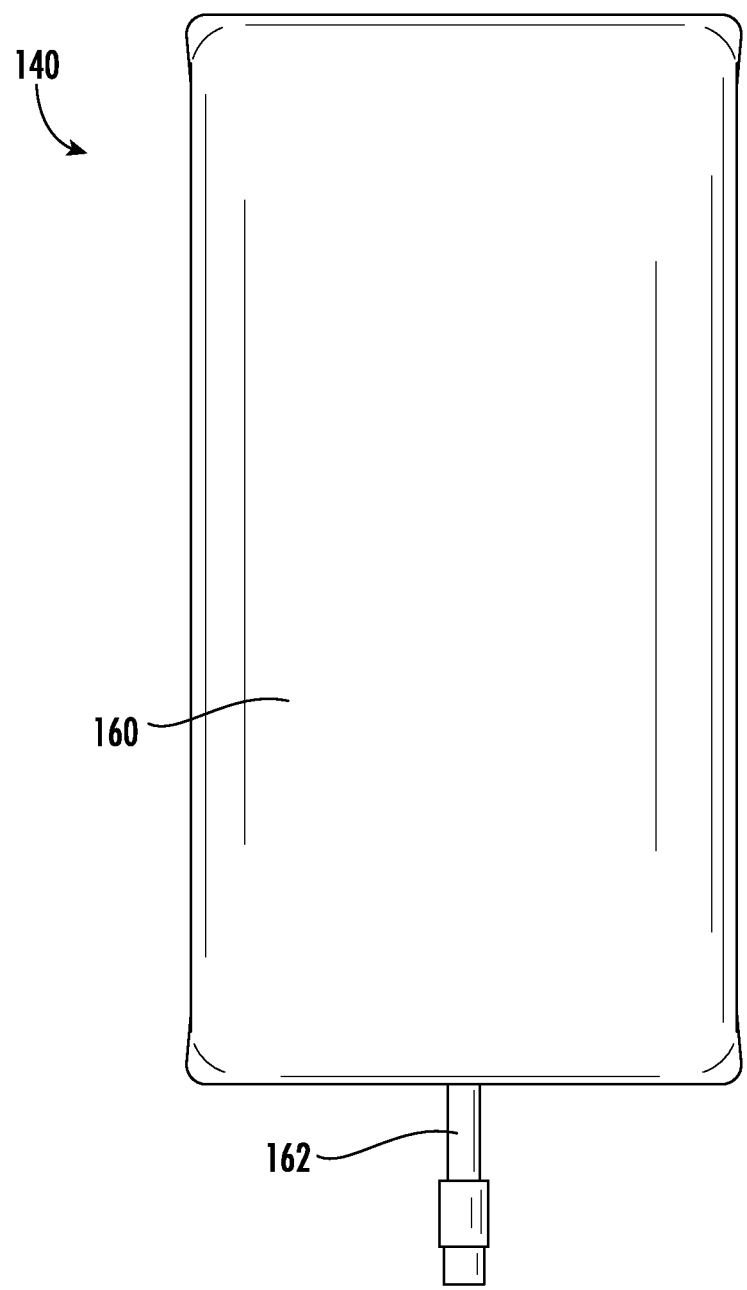
FIG. 2 illustrates a perspective view of a convention dialysate container or bag that can be used in the CAPD system of FIG. 1.

Referring to FIG. 2, the dialysate container 140 may be in the form of a bag, as will be readily appreciated and understood by one of ordinary skill in the art. As illustrated, the dialysate bag 140 includes a reservoir 160 arranged and configured to store fresh dialysate and an exit port 162 arranged and configured to couple to the tubing 144 to enable dialysate flow from the dialysate bag 140 to the catheter 120. In various embodiments, the dialysate bag 140 may include a frangible part or portion. As will be readily appreciated by one of ordinary skill in the art, the frangible part or portion prevents fluid flow from the dialysate bag 140 until the frangible part or portion is broken at the time of use.

As previously mentioned, contrary to manufacturer warnings, users have been known to heat the dialysate bag in a microwave oven, instead of the recommended warming box, a warming wrap, etc., to save time. However, heating a dialysate bag within a microwave oven can be dangerous. For example, utilization of a microwave to heat the dialysate bag may create hot spots within the dialysate. That is, although the dialysate bag may only feel warm to the patient's touch, a pocket could exist within the dialysate that is significantly hotter.

In accordance with one or more features of the present disclosure, a thermal protection system is provided. In use, the thermal protection system is arranged and configured to prevent, inhibit, indicate, etc. when the dialysate container (e.g., bag) 140 has been subjected to a temperature greater than a predetermined temperature such as, for example, when the dialysate bag has been placed within and heated by a microwave oven. In use, upon being subjected to temperatures greater than the predetermined temperature, the thermal protection system is arranged and configured to indicate and/or prevent (e.g., stop) usage of the dialysate containers.

In various embodiments, the thermal protection system is incorporated within the dialysate container (e.g., bag) 140. In one or more embodiments, the thermal protection system may be coupled to, operatively associated with, be part of, etc. the frangible part or portion of the dialysate container 140. For example, in one embodiment, the thermal protection system may be integrated into the frangible part such that upon reaching a predetermined temperature, the thermal protection system melts preventing the frangible part from being broken. Alternatively, in other embodiments, the thermal protection system may be anchored to the frangible part.

Figure 3A:
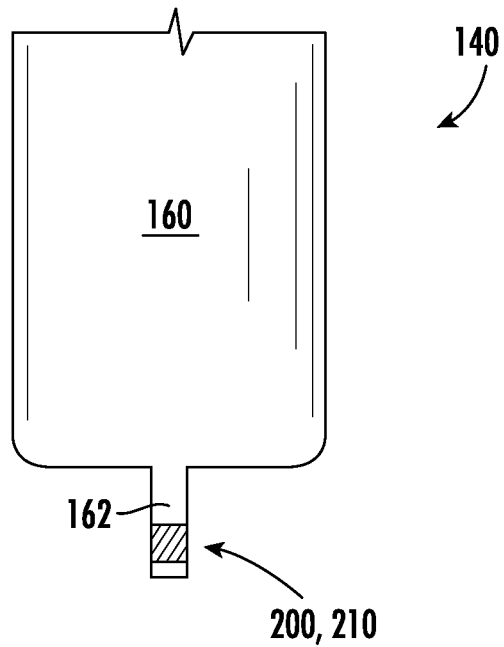
FIGS. 3A and 3B illustrate an example of an embodiment of a thermal protection system that may be incorporated into the dialysate container or bag of FIG. 2 in accordance with one or more features of the present disclosure.
Figure 3B:
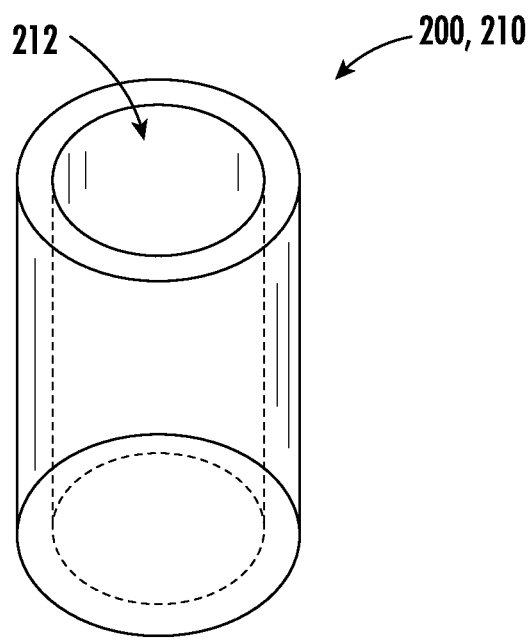

In one embodiment, referring to FIGS. 3A and 3B, the thermal protection system 200 is arranged and configured as a circular ring 210 manufactured from, for example, plastic. In use, the plastic ring 210 may be positioned within the exit port 162 of the dialysate container 140. In one embodiment, the plastic ring 210 includes a central borehole 212 arranged and configured to enable the dialysate to flow from the dialysate container 140. As such, in one embodiment, the plastic ring 210 may be arranged and configured as a hollow plug, although other configurations are envisioned.

During use, when the dialysate container 140 is heated to a temperature greater than a predetermined temperate (e.g., greater than 100° F.), the plastic ring 210 may melt. Upon melting, the plastic ring 210 blocks subsequent fluid flow and thus prevents further usage of the dialysate container 140 (e.g., circular ring 210 melts to block the borehole 212). In use, it should be understood and/or appreciated, that the thermal protection system 200 (e.g., plastic ring 210) need not require the heating of the entire dialysate container 140. Rather, upon reaching a predetermined temperature, the thermal protection system 200 (e.g., plastic ring 210) may melt thereby preventing fluid flow (e.g., upon microwaving of the thermal protection system 200 (e.g., plastic ring 210) to a predetermined temperature the thermal protection system 200 (e.g., plastic ring 210) would activate preventing fluid flow regardless if the entire dialysate container 140 was heated to the predetermined temperature or not).

In one embodiment, the plastic ring 210 may be mounted onto a support ring, which is arranged and configured with increased microwave absorbance (e.g., the support ring has an increased melting point such that the support ring does not melt when subjected to microwave radiation). Thus arranged, when the dialysate bag 140 is subjected to microwave radiation, the plastic ring 210 melts onto the support ring, which acts as a substrate to retain and guide the melted plastic ring 210 to block fluid flow. Alternatively, in another embodiment, the thermal protection system 200 may be arranged and configured so that when it melts, the thermal protection system 200 prevents the frangible portion from being broken. Thus arranged, the existing mechanism in the dialysate containers blocks fluid flow.

In use, while the circular ring 210 has been described as being manufactured from a plastic material, the circular ring 210 can be manufactured from any suitable material arranged and configured with a suitable melting point. Similarly, the support ring can be manufactured from any suitable material arranged and configured with a suitable melting point including, for example, a plastic. Alternatively, the support ring can be manufactured from a suitable material that upon reaching a predetermined temperature is arranged and configured to expand to close or block the exit port to block fluid flow. Subsequently, in one embodiment, upon cooling below the predetermined temperature, the support ring can shrink to once again enable fluid flow. Alternatively, the member may remain in the expanded configuration thus requiring the dialysate container to be discarded.

In one embodiment, a wrapping may also be provided. For example, a metallic or foil wrapping may be provided. In use, the metallic wrapping is arranged and configured to quickly receive the microwave absorbance. Upon receiving the microwave absorbance, the metallic wrapping quickly heats the circular or plastic ring 210 to ensure that the circular or plastic ring 210 is melted to prevent fluid flow. That is, thus arranged, the thermal protection system may incorporate a thin metallic layer specifically aimed at rapidly heating the circular or plastic ring 210 in order to ensure that even a brief or short attempt to microwave the dialysate container renders the dialysate container unusable.

In one embodiment, the thermal protection system 200 may be in the form of or include a filter-like matrix containing a plurality of openings or holes (e.g., a filter with a grid pattern of openings or holes). In use, the openings or holes may be sufficiently large to allow dialysate to free flow under normal usage. In use, however, the filter may include a matrix of meltable material. Upon reaching a predetermined temperature, the matrix of meltable material melts sealing the opening or holes formed in the filter to thereby prevent fluid flow.

Alternatively, and/or in addition, in another embodiment, the thermal protection system 200 may be in the form of, or include, a thermally sensitive dye. In use, upon being subjected to higher temperatures, instead of, or in addition to, melting, the thermal protection system 200 could be arranged and configured to change color. Thus arranged, the thermal protection system 200 is arranged and configured to provide indication that the dialysate container 140 should not be used. For example, in one embodiment, the circular or plastic ring 210 may be arranged and configured to change color, instead of, or in addition to, melting, upon reaching a predetermined temperature. Alternatively, in one embodiment, the dialysate container 140 may incorporate, for example, a plastic frangible part or portion that may be arranged and configured to change color upon being subjected to a predetermined temperature. In addition, by properly tuning the thermal protection system 200, the thermal protection system 200 can be used to determine if the dialysate container 140 is stored appropriately such that, for example, if the dialysate container has been subjected to temperatures that exceed acceptable storage safety limits, the thermal protection system 200 can change color, thus indicating that the dialysate container 140 should no longer be used. In one embodiment, the dye may be incorporated into a portion of a plastic or plastic container, preferably that is not visible during normal usage, but upon reaching a predetermined temperature melts causing the dye to appear and/or be released. Alternatively, in another embodiment, the dye itself may be arranged and configured to be thermally sensitive such that it has little or no color, but once heated to the predetermined temperature undergoes a chemical reaction that creates a color change.

Figure 4A:
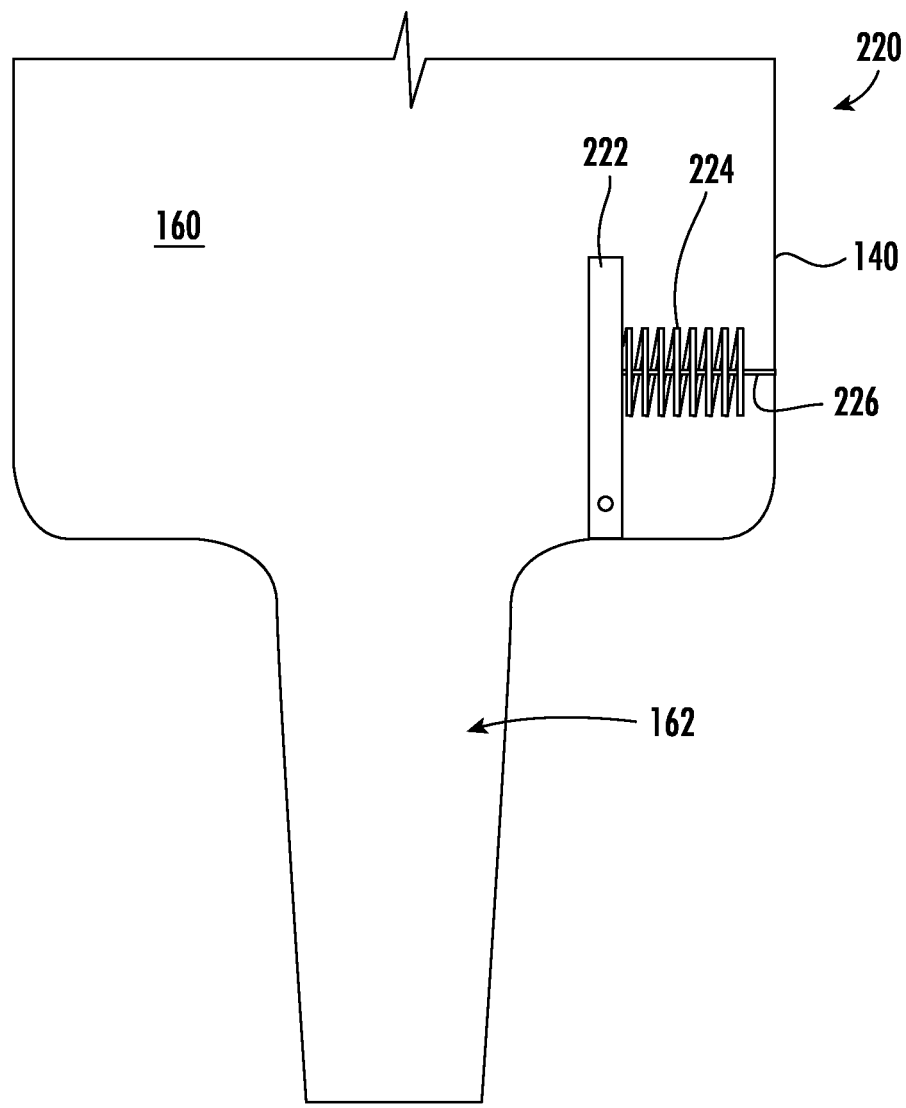
FIG. 4A illustrates an alternate example embodiment of a thermal protection system that may be incorporated into the dialysate container or bag of FIG. 2 in accordance with one or more features of the present disclosure.
Figure 4B:
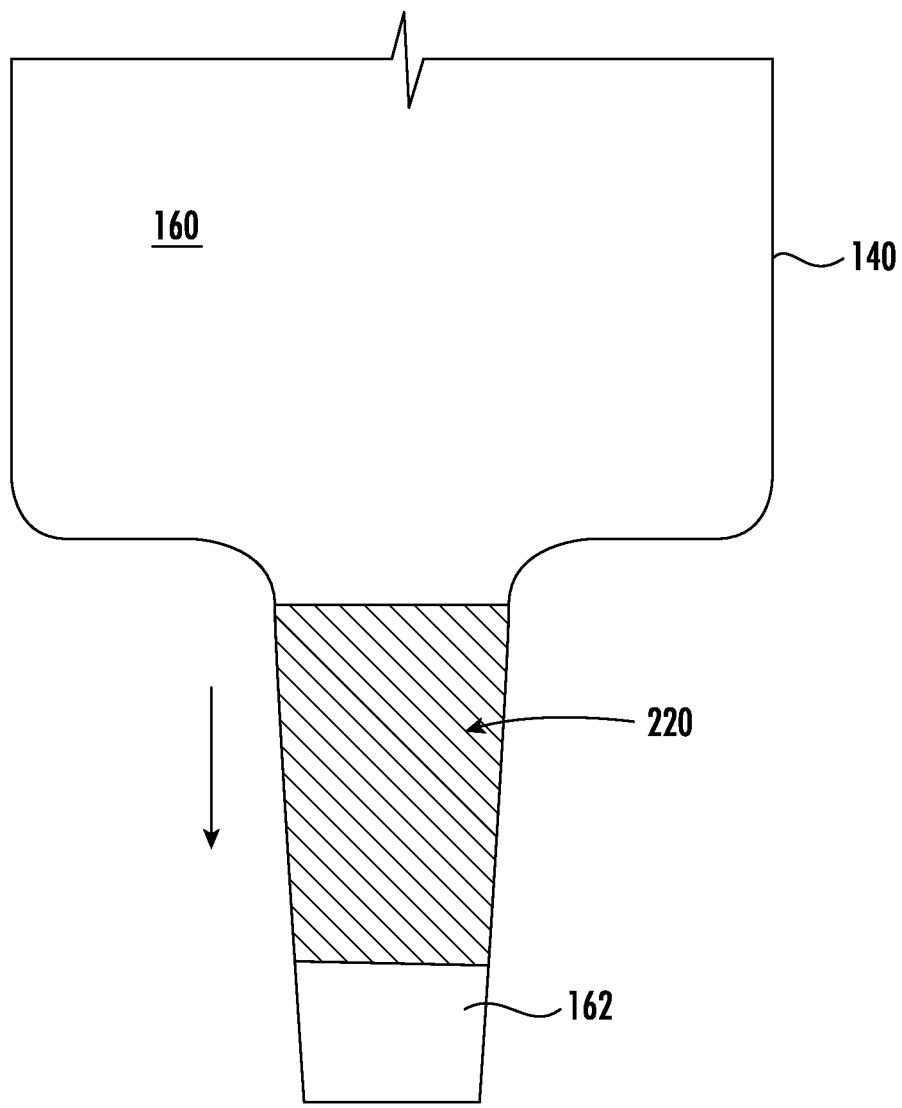
FIGS. 4B-4D illustrate alternate example embodiments of a thermal protection system that may be incorporated into the dialysate container or bag of FIG. 2 in accordance with one or more features of the present disclosure.
Figure 4C:
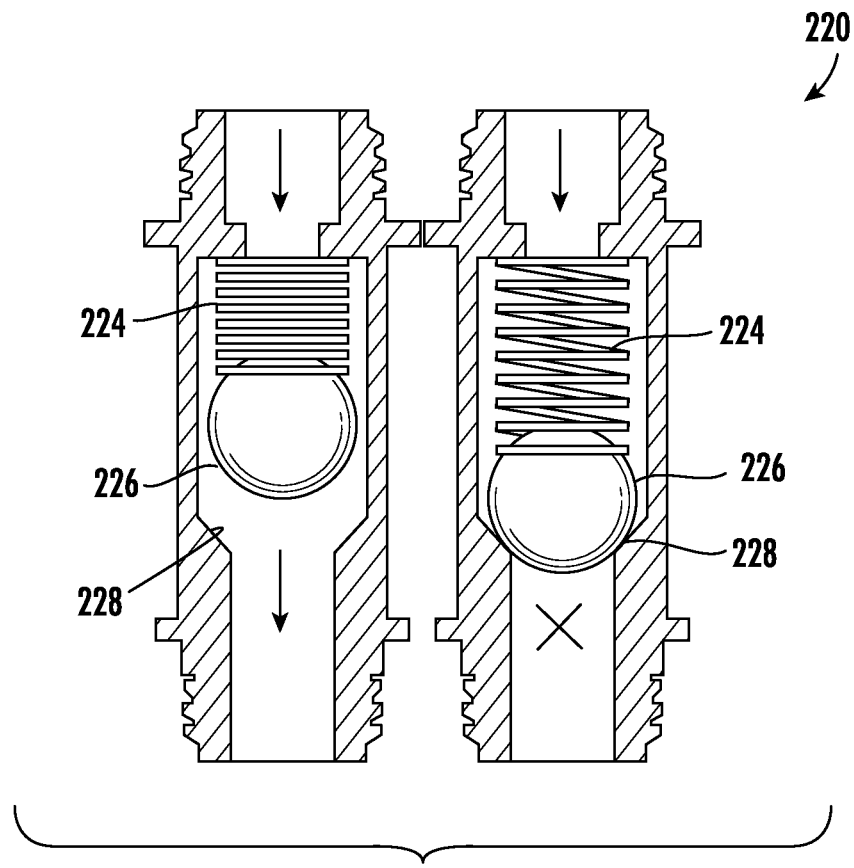
Figure 4D:
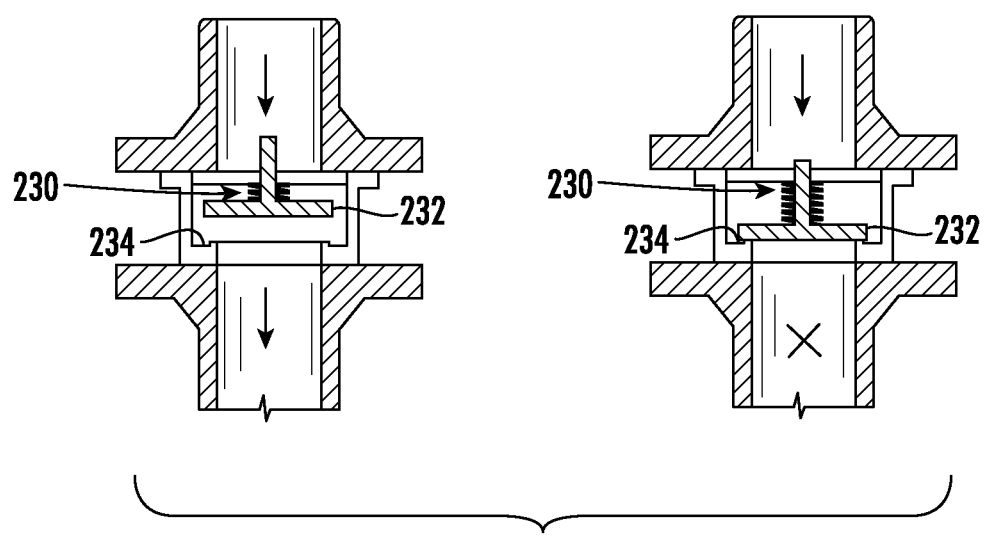

Alternatively, referring to FIGS. 4A and 4B, in one embodiment, the thermal protection system 200 may be arranged and configured as a spring-loaded plunger. In use, the spring-loaded plunger 220 may include a plunger member or valve member 222, a spring 224, and a holding member 226. Upon being subjected to a predetermined temperature, the holding member 226 melts, which releases the spring 224 causing the plunger member or valve 222 to block the exit port 162. For example, referring to FIG. 4A, the plunger member 222 may be arranged and configured to pivot to block the exit port 162. That is, the plunger member 222 may be pivotable from a first position enabling the fresh dialysate to flow through the exit port 162 and into the tubing, to a second position blocking the fresh dialysate from flowing through the exit port 162 and into the tubing. Alternatively, referring to FIGS. 4B and 4C, the plunger member 222 may be arranged and configured to be vertically displaceable to block the exit port 162. In use, the vertically displaced spring-loaded plunger may be any system now known or hereafter developed whereby in a first position fluid flow is enabled and in a second position fluid flow is prevented. For example, as illustrated in FIG. 4C, the spring loaded plunger 220 may be arranged and configured as a spring-loaded ball check valve including a spring 224 and a ball 226 wherein, in a first position, the spring 224 is maintained in a compressed configuration by, for example, a holding member (e.g., a plastic member that holds the spring 224 in its compressed state but upon reaching a predetermined temperature melts thereby releasing the spring 224). However, upon reaching a predetermined temperature, the holding member releases the spring 224 thereby moving the ball 226 into abutting contacting with an internal wall 228 of the spring-loaded plunger 220 to thereby prevent fluid flow. Alternatively, referring to FIG. 4D, the spring loaded plunger 220 may be arranged and configured as a spring-loaded plate including a spring 230 and a plate 232 wherein, in a first position, the spring 230 is maintained in a compressed configuration by, for example, a holding member. However, upon reaching a predetermined temperature, the holding member releases the spring 230 thereby moving the plate 230 into abutting contacting with an internal wall or shoulder 234 of the spring-loaded plunger 220 to thereby prevent fluid flow. In either embodiment, the spring loaded plunger 220 may be vertically displaceable from a first position enabling the fresh dialysate to flow through the exit port and into the tubing, to a second position blocking the fresh dialysate from flowing through the exit port and into the tubing. Alternatively, in other embodiments, non-spring loaded systems may be used. For example, in one embodiment, a plug may be utilized wherein in a first configuration the plug is sized and configured to enable fluid flow. However, upon reaching a predetermined temperature, the plug may be sized and configured to permanently expand to block the exit port and thus prevent fluid flow.

As used herein, an element or operation recited in the singular and proceeded with the word "a" or "an" should be understood as not excluding plural elements or operations, unless such exclusion is explicitly recited. Furthermore, references to "one embodiment" of the present disclosure are not intended to be interpreted as excluding the existence of additional embodiments that also incorporate the recited features.

The foregoing discussion has been presented for purposes of illustration and description and is not intended to limit the disclosure to the form or forms disclosed herein. For example, various features of the disclosure are grouped together in one or more aspects, embodiments, or configurations for the purpose of streamlining the disclosure. However, it should be understood that various features of the certain aspects, embodiments, or configurations of the disclosure may be combined in alternate aspects, embodiments, or configurations. In addition, while certain embodiments have been described and illustrated with certain features, it is envisioned that features of one embodiment may be used in combination with other embodiments. Moreover, the following claims are hereby incorporated into this Detailed Description by this reference, with each claim standing on its own as a separate embodiment of the present disclosure.

The present disclosure is not to be limited in scope by the specific embodiments described herein. Indeed, other various embodiments of and modifications to the present disclosure, in addition to those described herein, will be apparent to those of ordinary skill in the art from the foregoing description and accompanying drawings. Thus, such other embodiments and modifications are intended to fall within the scope of the present disclosure. Furthermore, although the present disclosure has been described herein in the context of a particular implementation in a particular environment for a particular purpose, those of ordinary skill in the art will recognize that its usefulness is not limited thereto and that the present disclosure may be beneficially implemented in any number of environments for any number of purposes. Accordingly, the claims set forth below should be construed in view of the full breadth and spirit of the present disclosure as described herein.

What is claimed is:

1. A dialysate container, comprising:
a reservoir arranged and configured to store dialysate;
an exit port arranged and configured in fluid communication with the reservoir and arranged and configured to couple to tubing so that dialysate can flow from the reservoir to the tubing; and
a circular hollow ring positioned within the exit port of the dialysate container, the circular hollow ring arranged and configured in operative communication with the exit port so that dialysate may flow from the reservoir through the circular hollow ring to the tubing, the circular hollow ring being arranged and configured so that when the dialysate container is subjected to a temperature greater than a predetermined temperature, the circular hollow ring melts upon reaching the predetermined temperature to block a borehole of the circular hollow ring to prevent the dialysate from flowing through the exit port and into the tubing.

2. The dialysate container of claim 1, wherein the circular ring comprises a plastic material.

3. The dialysate container of claim 1, further comprising a support ring having a melting temperature greater than the predetermined temperature so that the support ring guides the melted circular hollow ring to block the dialysate from flowing through the exit port and into the tubing.

4. The dialysate container of claim 3, wherein the support ring is arranged and configured to expand to close or block the exit port and remain in an expanded configuration.

5. The dialysate container of claim 1, further comprising a thermally sensitive dye arranged and configured to change color upon being subjected to the predetermined temperature to indicate that the dialysate container has been subjected to a temperature greater than the predetermined temperature.

6. The dialysate container of claim 5, wherein the thermally sensitive dye is incorporated into a frangible part of the dialysate container.

7. The dialysate container of claim 1, wherein the circular hollow ring is configured to change color upon being subjected to the predetermined temperature.

8. A dialysate container, comprising:
a reservoir arranged and configured to store dialysate;
an exit port arranged and configured in fluid communication with the reservoir and arranged and configured to couple to tubing so that dialysate can flow from the reservoir to the tubing; and
a circular hollow ring positioned within the exit port of the dialysate container so that dialysate may flow from the reservoir through the circular hollow ring to the tubing, the circular hollow ring arranged and configured so that when the dialysate container is subjected to a temperature greater than a predetermined temperature, the circular hollow ring melts to block a borehole of the circular hollow ring to prevent the dialysate from flowing through the exit port and into the tubing, or to indicate that the dialysate container has been subjected to a temperature greater than the predetermined temperature, or a combination thereof;
wherein the circular hollow ring is configured to change color upon being subjected to the predetermined temperature.

9. The dialysate container of claim 8, wherein the circular ring comprises a plastic material.

10. The dialysate container of claim 8, wherein the circular ring is arranged and configured to melt upon reaching the predetermined temperature, the melted circular ring blocking the dialysate from flowing through the exit port and into the tubing.

11. The dialysate container of claim 10, further comprising a support ring having a melting temperature greater than the predetermined temperature so that the support ring guides the melted circular ring to block the dialysate from flowing through the exit port and into the tubing.

12. The dialysate container of claim 11, wherein the support ring is arranged and configured to expand to close or block the exit port and remain in an expanded configuration.

13. The dialysate container of claim 8, further comprising a thermally sensitive dye arranged and configured to change color upon being subjected to the predetermined temperature to indicate that the dialysate container has been subjected to a temperature greater than the predetermined temperature.

14. The dialysate container of claim 13, wherein the thermally sensitive dye is incorporated into a frangible part of the dialysate container.

* * * * *